Dec. 6, 1966 C. H. FISCHER Plant Pat. 2,690
GLADIOLUS PLANT
Filed Sept. 7, 1965
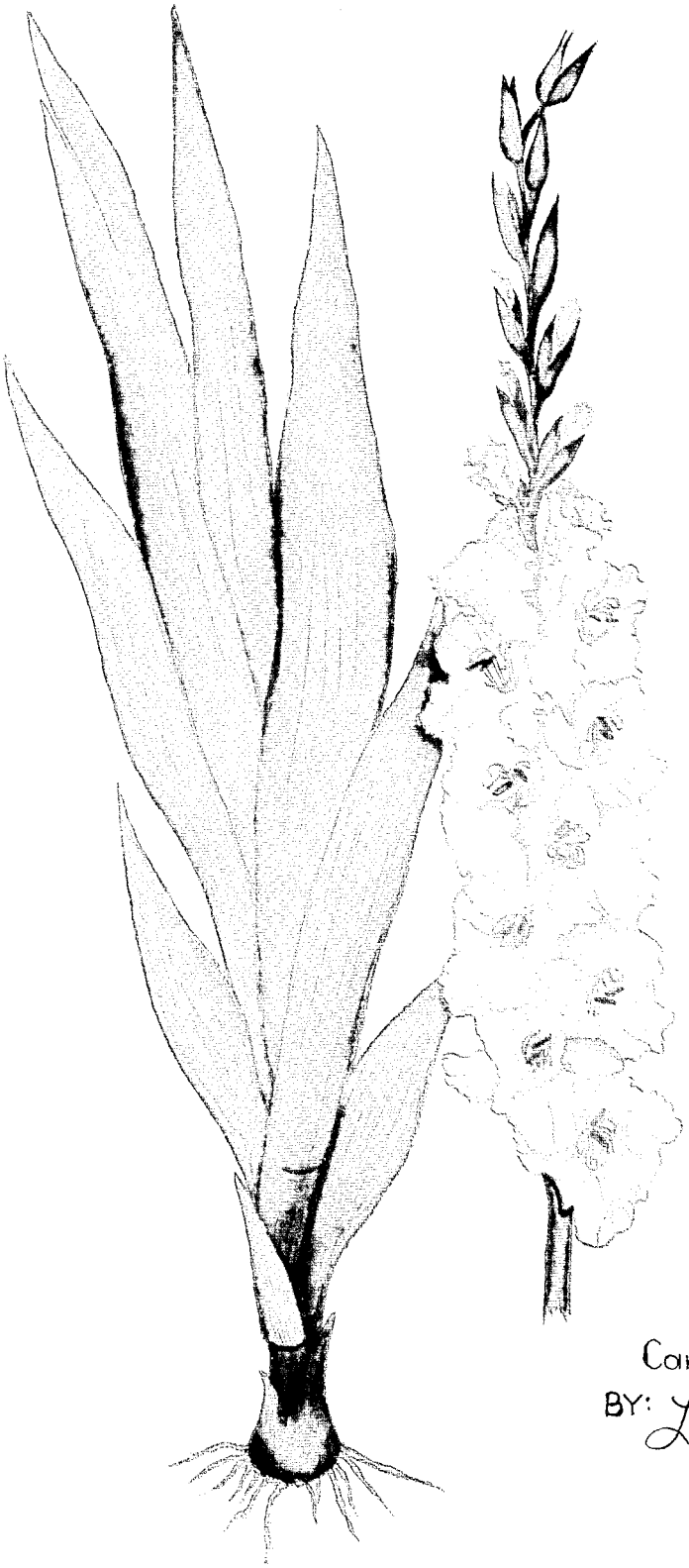
INVENTOR
Carl H. Fischer
BY: Lamont Johnston
ATTORNEY United States Patent Office Plant Pat. 2,690
Patented Dec. 6, 1966

2,690
GLADIOLUS PLANT

Carl H. Fischer, St. Charles, Minn., assignor to Selected Glads, Inc., New Albany, Ind., a corporation of Tennessee Filed Sept. 7, 1965, Ser. No. 485,660
1 Claim. (Cl. Plt.—85)

My present invention relates to a new and improved variety of gladiolus plant and is notable particularly for its rugged plant, consistent performance, long flowerhead, ruffling, lovely color and greenish throat of its blossom. I have identified this new variety as seedling #248-60 in my breeding work.

To the best of my knowledge, this new variety is the result of a cross between a seedling (unpatented) and an unknown variety. Hand cross pollination was done by me in my field at St. Charles, Minnesota, but no precaution was taken to prevent admixture of other varieties by bees or insects.

The new variety has been asexually reproduced by me in Minnesota and California by natural increase from cormels through several generations and its characteristics have proven to be permanently fixed.

The illustration, made a part of this application, shows a single bloom spike and plant of this variety, reduced in size, and is as nearly true to color as it is possible to depict. The illustration shows the color, form and placement on the spike.

In the following detailed description, color plate references are to "The Horticultural Colour Chart," by the British Colour Council. Where there are other references to color, the ordinary dictionary meanings of the terms are intended.

*The plant*

Growth: Extremely rugged. Plant averages 60 to 65 inches in height over-all. Propagates very well.

Blooming: This variety blooms in late mid-season, coming into bloom in about 90 days from large bulbs in the north.

Stems: Sturdy and straight. Diameter at base of cutting stem is ⅜ inch. Color of stem above the bulb is rosy purple.

Foliage: Deep, healthy green; leaves are broad and fan shaped on the plant. Plant foliage, excluding the flower spike, is 34 inches in height and has upright leaves.

Disease resistance: This variety is unusually resistant to common diseases which affect many gladiolus varieties.

Corms: Round, plump and smooth; high crowned with excellent husk covering. Husk has a purplish color which is deeper toward the top of the corm. Color of flesh is Maize Yellow $607/_1$.

*The flower*

Spike: Tall, with 20 to 25 buds of which 8 to 10 are open at one time with 8 showing color.

Bud:

*Size.*—Opening buds are 2½ inches long.

*Opening.*—Eight will show color at one time.

Flower:

*Arrangement.*—The florets are placed in a formal, double row on the spike and all usually face forward.

*Size.*—Individual florets measure 4½ to 5 inches in diameter. Upper blooms are progressively smaller.

*Form.*—Florets are somewhat triangular and close together on the spike. They are wide open and slightly recurved at outer edges.

*Keeping qualities.*—Keeps and opens well.

Petals:

*Shape.*—Rounded and ruffled at the edges. Upper petal curves in toward the throat.

*Size.*—Outer petals are 1½ inches across; lip petal is 1 inch.

*Aspect.*—Substance is average. Surface is uneven and ruffled.

*Fragrance.*—None.

*Color.*—Largest area is Sulphur Yellow $1/_3$ to $1/_2$ at the edges. Lip petal is Sulphur Yellow 1. In the throat the color is Primrose Yellow 601.

Reproductive organs:

*Stamens.*—Light purple.

*Pistil.*—Cream.

*Comparisons*

My new variety resembles Ruffles (Plant Patent No. 2,361) more than any other variety, but differs from it principally as follows:

(1) This variety is deeper in color; has a contrasting throat.

(2) This variety has a longer flowerhead and more buds.

(3) This variety has a straighter stem.

(4) This variety opens more florets at one time and shows more color in the buds.

Having thus disclosed my invention, I claim:

The new and distinct variety of gladiolus plant, substantially as herein shown and described, characterized by its rugged plant, consistent performance, long flowerhead, ruffling, lovely color and greenish throat of its blossom.

No references cited.

ABRAHAM G. STONE, *Primary Examiner.*

R. E. BAGWILL, *Assistant Examiner.*